(12) United States Patent
Cree et al.

(10) Patent No.: US 6,849,319 B2
(45) Date of Patent: Feb. 1, 2005

(54) APERTURED NONWOVEN COMPOSITES AND METHOD FOR MAKING

(75) Inventors: James W. Cree, Chesterfield, VA (US); Lino Iulianetti, Torre dei Passeri (IT); Antonietta Splendiani, Pescara (IT)

(73) Assignee: Tredegar Film Products Corporation, Richmond, VA (US)

(*) Notice: Subject to any disclaimer, the term of this patent is extended or adjusted under 35 U.S.C. 154(b) by 35 days.

(21) Appl. No.: 10/308,312

(22) Filed: Dec. 2, 2002

(65) Prior Publication Data

US 2003/0124311 A1 Jul. 3, 2003

Related U.S. Application Data

(60) Provisional application No. 60/336,918, filed on Dec. 3, 2001.

(51) Int. Cl.[7] .................................................. B32B 5/02
(52) U.S. Cl. ........................ 428/138; 428/137; 604/358; 604/365; 604/385.101
(58) Field of Search ................................. 428/137, 138; 604/358, 365, 385.101, 366, 378, 385.11

(56) References Cited

U.S. PATENT DOCUMENTS

| | | | |
|---|---|---|---|
| RE26,152 E | 1/1967 | K.H. Andren | |
| 3,860,003 A | 1/1975 | Buell | 128/287 |
| 3,929,135 A | 12/1975 | Thompson | 128/287 |
| 3,967,623 A | 7/1976 | Butterworth et al. | 128/287 |
| 4,128,679 A | 12/1978 | Pohland | 428/131 |
| 4,253,461 A | 3/1981 | Strickland et al. | 128/287 |
| 4,285,343 A | 8/1981 | McNair | 128/287 |
| 4,342,134 A | 8/1982 | Mickelson | 16/31 |
| 4,342,314 A | 8/1982 | Radel et al. | 128/287 |
| 4,456,570 A | 6/1984 | Thomas et al. | 264/22 |
| 4,589,876 A | 5/1986 | Van Tilburg | 604/385 |
| 4,597,760 A | 7/1986 | Buell | 604/397 |

(List continued on next page.)

FOREIGN PATENT DOCUMENTS

| | | |
|---|---|---|
| CA | 888304 | 12/1971 |
| EP | 0 165 807 A | 12/1985 |
| EP | 0 214 608 A2 | 3/1987 |
| EP | 0 472 992 A1 | 3/1992 |
| EP | 0 573 277 B1 | 4/1996 |
| EP | 0 472 922 B1 | 5/1996 |
| EP | 0 749 738 A | 12/1996 |
| EP | 0 995 414 A1 | 4/2000 |
| EP | 1 001 064 | 5/2000 |

OTHER PUBLICATIONS

PCT International Search Report, reviewed by Anne Henningsen, May 6, 2003.

*Primary Examiner*—Harold Pyon
*Assistant Examiner*—Alicia Chevalier
(74) *Attorney, Agent, or Firm*—Fish & Richardson P.C.

(57) ABSTRACT

An absorbent article has a body facing side which is positioned against the users body. The absorbent article is made of, at least, a backsheet, an absorbent core, and a composite topsheet. The backsheet is opposite the body facing side. The absorbent core is between the backsheet and the body facing side. The composite topsheet is between the absorbent core and the body facing side. The composite topsheet includes a resilient three dimensional apertured formed film, a nonwoven web small scale apertures, and large scale apertures. The formed film is between the absorbent core and the body facing side. The formed film has a male side and a female side opposite the male side, and small scale apertures with a mesh count. The nonwoven web of fibers is between the formed film and the body facing side of the absorbent article. The large scale apertures extend through the nonwoven web and the formed film. The large scale apertures have a mesh count which is less than the mesh count of the small scale apertures.

33 Claims, 2 Drawing Sheets

U.S. PATENT DOCUMENTS

| | | | |
|---|---|---|---|
| 4,597,761 A | 7/1986 | Buell .......................... 604/397 |
| 4,610,678 A | 9/1986 | Weisman et al. ........... 604/368 |
| 4,629,643 A | 12/1986 | Curro et al. ................. 428/131 |
| 4,673,402 A | 6/1987 | Weisman et al. ........... 604/368 |
| 4,687,478 A | 8/1987 | Van Tilburg ................ 604/387 |
| 4,695,278 A | 9/1987 | Lawson ....................... 604/385 |
| 4,704,115 A | 11/1987 | Buell .......................... 604/385 |
| 4,738,676 A | 4/1988 | Osborn, III ................. 604/385 |
| 4,741,941 A | 5/1988 | Englebert et al. ............. 428/71 |
| 4,758,297 A | 7/1988 | Calligarich ................. 156/251 |
| 4,820,294 A | 4/1989 | Morris |
| 4,834,735 A | 5/1989 | Alemany et al. ........... 604/368 |
| 4,886,632 A | 12/1989 | Van Iten et al. ............ 264/156 |
| 4,888,231 A | 12/1989 | Angstadt .................... 428/213 |
| 4,909,802 A | 3/1990 | Ahr et al. ................. 604/385.1 |
| 4,909,803 A | 3/1990 | Aziz et al. ............... 604/385.2 |
| 4,917,697 A | 4/1990 | Osborn, III et al. ........ 604/387 |
| 4,950,264 A | 8/1990 | Osborn, III ............. 604/385.1 |
| 4,964,860 A | 10/1990 | Gipson et al. .............. 604/391 |
| 5,007,906 A | 4/1991 | Osborn, III et al. ..... 604/385.1 |
| 5,009,653 A | 4/1991 | Osborn, III ................. 604/385 |
| 5,188,625 A | 2/1993 | Van Iten et al. ............ 604/383 |
| 5,223,319 A | 6/1993 | Cotton et al. ............... 428/131 |
| 5,429,854 A | 7/1995 | Currie et al. ............... 428/138 |
| 5,560,794 A | 10/1996 | Currie et al. ............... 156/73.2 |
| 5,573,719 A | 11/1996 | Fitting ........................ 264/129 |
| H01670 H | * 7/1997 | Aziz et al. .................. 604/367 |
| 5,667,619 A | 9/1997 | Alikhan ...................... 156/253 |
| 5,667,625 A | 9/1997 | Alikhan ...................... 156/553 |
| 5,817,394 A | 10/1998 | Alikhan et al. ............. 428/137 |
| 5,858,504 A | 1/1999 | Fitting ........................ 428/131 |
| 6,022,608 A | 2/2000 | Dell 'Acqua ............... 428/132 |
| 6,117,524 A | * 9/2000 | Hisanaka et al. ........... 428/137 |
| 6,168,849 B1 | 1/2001 | Braverman et al. ......... 428/137 |
| 6,231,948 B1 | 5/2001 | Ouellette et al. |
| 6,582,798 B2 | 6/2003 | Thomas |
| 6,610,391 B2 | 8/2003 | Molee |
| 6,686,512 B2 | 2/2004 | Herrlein et al. |

FOREIGN PATENT DOCUMENTS

| | | | |
|---|---|---|---|
| EP | 1 046 479 A1 | 10/2000 | |
| EP | 1 048 419 | 11/2000 | |
| GB | 2 272 917 | 6/1994 | |
| JP | 10-80968 A | * 3/1998 | ............. B32B/5/02 |
| WO | WO 99/25550 | 5/1999 | |
| WO | WO 00/34562 | 6/2000 | |
| WO | WO 01/32417 | 5/2001 | |
| WO | WO 02/090106 | 11/2002 | |

* cited by examiner

APERTURED NONWOVEN COMPOSITES AND METHOD FOR MAKING

This application claims the benefit of Provisional Application No. 60/336,918, filed Dec. 3, 2001.

BACKGROUND OF THE INVENTION

1. Technical Field of the Invention

This invention relates to nonwoven composites and particularly to nonwoven composites used in absorbent articles.

2. Description of Related Art

There are several known topsheets formed of either nonwoven materials or formed films that have been designed to handle viscous exudate such as new born infant stool or viscous menses fluid. These topsheet materials specifically have large apertures and the nonwoven products have a cloth like texture while the film products have a flat sticky surface. Formed films are typically known to have better absorbency rates and wetback properties, but nonwovens tend to be softer and gentler to the skin.

Attempts to use topsheets with large apertures has met with limited success due to the nature of the large holes. In the case of nonwovens, the large holes were two-dimensional because the soft fibers used were not sufficiently resilient to support the three dimensional structure. In the case of formed films, the material which were three dimensional and resilient enough to maintain this shape were too rigid and not soft on the wearers' skin.

Newborn infants, especially those being fed breast milk, are known to have a more fluid stool and to have explosive bowel movements due to excess gas in their sensitive systems. The combination of a fluid stool and explosive bowel movements presents a technical problem for known topsheet materials. The topsheet must have exceptionally high acquisition rates to capture the fast moving stool as it travels across the diaper. Furthermore, the topsheet must have good, wetback properties to maintain the fluid stool in the absorbent core after repeated insults.

Nonwovens and films have been designed to meet one or the other of these design criteria, yet parents still know that these explosive newborn bowel movements will likely escape all known diapers and therefore soil the infant's clothing, the parent's clothing, and bedding materials.

Similar performance criteria would be advantageous in feminine hygiene products as well.

It would be advantageous to have a topsheet with an exceptional absorbency rate while still maintaining acceptable wetback properties.

SUMMARY OF THE INVENTION

An absorbent article has a body facing side which is positioned against the user's body. The absorbent article is made of, at least, a backsheet, an absorbent core, and a composite topsheet. The backsheet is opposite the body facing side. The absorbent core is between the backsheet and the body facing side. The composite topsheet is between the absorbent core and the body facing side. The composite topsheet includes a resilient three dimensional apertured formed film, a nonwoven web and large scale apertures. The formed film is between the absorbent core and the body facing side. The formed film has a male side and a female side opposite the male side, and small scale apertures with a mesh count. The nonwoven web of fibers is between the formed film and the body facing side. The large scale apertures extend through the nonwoven web and the formed film. The large scale apertures have a mesh count which is less than the mesh count of the small scale apertures.

The formed film may be positioned with its male side facing the body facing side of the absorbent article or with its female side facing the body facing side of the absorbent article.

The formed film may be replaced with a stiffer nonwoven layer with fibers of larger average radius than the nonwoven web.

A preferred embodiment of the composite topsheet is formed with an apparatus using heated pins and shaped holes.

One advantage of this invention is that the large scale apertures trap the fast moving fluids and direct them to the absorbent core. Additionally, the small scale apertures allow fluid between the large scale apertures to pass into the absorbent core, while the void between the formed film and the nonwoven layer helps to direct fluids toward the large scale apertures. All of these features contribute to excellent absorbency rate performance. At the same time, the shape of the large scale apertures, the formed film between the large scale apertures, and the void volume between the composite topsheet and the absorbent core, all help to prevent wetback.

Furthermore, the void volume between the composite topsheet and the absorbent core contributes to both absorbency rate and wetback. In this invention, absorbency rates are reduced significantly while wetback rates are improved either substantially or at least moderately as compared to the known art. In particular, the resilient nature of the large scale apertures, as supported by the resilient film or coarse nonwoven layer, allows the three-dimensional large scale aperture to maintain its shape during processing, storage and use so that the void volume is maintained.

These advantages are also applicable to the feminine hygiene field, as is shown below in the test data.

DETAILED DESCRIPTION OF THE EXEMPLARY EMBODIMENTS OF THE INVENTION

Definitions

Figure 1:
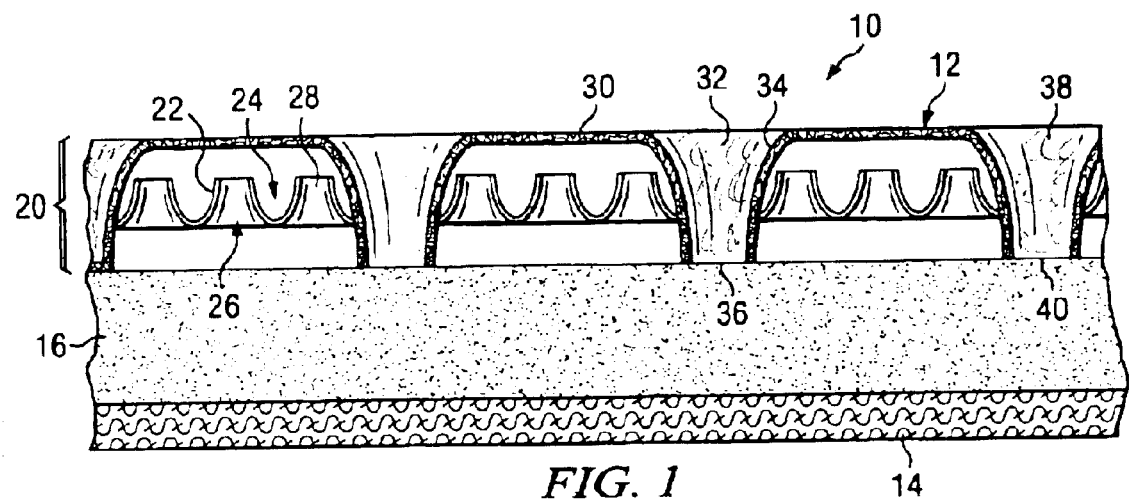
FIG. 1 is a cross sectional view of a first embodiment of the absorbent article of the invention.

As used herein, the term "substantially" means that a given property or parameter may vary by about 20% from the stated value.

As used herein, the term "absorbent article" means articles that absorb and contain body exudates. More specifically, the term refers to articles which are placed against or in proximity to the body of a wearer for absorbing and containing various exudates discharged from the body. For example, "absorbent article", as used herein, includes diapers, incontinent articles, sanitary napkins, pantiliners, bandages, and other articles used to absorb body exudates.

The term "diaper" refers to a garment typically worn by infants and incontinent persons that is drawn up between the legs and fastened about the waist of the wearer. Examples of diapers from the prior art include diapers described in U.S. Pat. Re. No. 26,152, issued to Duncan, et al. on Jan. 31, 1967; U.S. Pat. No. 3,860,003 issued to Buell on Jan. 14, 1975; U.S. Pat. No. 4,610,678 issued to Weisman, et al. on Sep. 9, 1986; U.S. Pat. No. 4,673,402 issued to Weisman, et al. on Jun. 16, 1987; U.S. Pat. No. 4,695,278 issued to Lawson on Sep. 22, 1987; U.S. Pat. No. 4,704,115 issued to Buell on Nov. 3, 1987; U.S. Pat. No. 4,834,735 issued to Alemany, et al. on May 30, 1989; U.S. Pat. No. 4,888,231 issued to Angstadt on Dec. 19, 1989; and U.S. Pat. No. 4,909,803 issued to Aziz, et al. on Mar. 20, 1990.

The term "incontinent article" refers to pads, undergarments, e.g., pads held in place by a suspension system, such as a belt, or other device, inserts for absorbent articles, capacity boosters for absorbent articles, briefs, bed pads, and similar devices, whether worn by adults or other incontinent persons. Examples of incontinent articles include those disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. Nos. 4,704,115; 4,909,802 issued to Ahr, et al.; U.S. Pat. No. 4,964,860 issued to Gipson, et al. on Oct. 23, 1990; and in U.S. patent application Ser. Nos. 07/637,090 and 07/637,571 filed respectively by Noel, et al. and Feist, et al. on Jan. 3, 1991.

The term "pantiliner" refers to absorbent articles that are less bulky than sanitary napkins that are generally worn by women between their menstrual periods. Examples of pantiliners are disclosed in U.S. Pat. No. 4,738,676 entitled "Pantiliner" issued to Osborn on Apr. 19, 1988.

The term "sanitary napkin" refers to an article that is worn by a female adjacent to the pudendal region that is intended to absorb and contain various exudates which are discharged from the body, e.g., blood, menses, and urine. Examples of sanitary napkins are disclosed in U.S. Pat. No. 4,285,343, issued to McNair on Aug. 25, 1981; U.S. Pat. Nos. 4,589,876 and 4,687,478, issued to Van Tilburg on May 20, 1986 and Aug. 18, 1987 respectively; U.S. Pat. Nos. 4,917,697 and 5,007,906 issued to Osborn, et al. on Apr. 17, 1990 and Apr. 16, 1991, respectively; and U.S. Pat. Nos. 4,950,264, and 5,009,653 issued to Osborn on Aug. 21, 1990 and Apr. 23, 1991, respectively; and in U.S. patent application Ser. No. 07/605,583 filed Oct. 29, 1990 in the name of Visscher, et al.

Throughout this description, the expressions "topsheet" and "backsheet" denote the relationship of these materials or layers with respect to the absorbent core. It is understood that additional layers may be present between the absorbent core and the topsheet and backsheet, and that additional layers and other materials may be present on the side opposite the absorbent core from either the topsheet or the backsheet.

As used herein, the term "formed film" refers to a resilient three dimensionally formed film similar in structure to that produced by vacuum forming processes, as described in U.S. Pat. No. 4,456,570 to Thomas or U.S. Pat. No. 3,929,135 to Thompson, among others.

As used herein, the term "non-woven web" refers to a web that has a structure of individual fibers or threads which are interlaid, but not in any regular, repeating manner. Non-woven webs have been, in the past, formed by a variety of processes such as, for example, meltblowing processes, spunbonding process, and bonded carded web processes.

As used herein, the term "meltblown fibers", refers to fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which may be to a microfiber diameter. Thereafter, the meltblown fibers are carried by the high velocity gas stream and are deposited on a collecting surface to form a web of randomly dispersed meltblown fibers.

As used herein, the term "stabilized" refers to a material of the present invention which is capable of being stored in a stable condition in any common or conventional web storage manner without the need for further heating or the additional of or joinder with other webs to stabilize the material. Such storage means would include for example, low tension rolls or festooned material in boxes.

As used herein, the term "melt-stabilized" refers to portions of a nonwoven web which have been subjected to localized heating and/or localized pressure to substantially consolidate the fibers of the nonwoven web into a stabilized film-like form.

As used herein, "pressure bonding" refers to a process in which a web is placed between two elements which exert pressure on the web to bind the various components of the web in the area where pressure is being exerted.

As used herein, the term "spunbonded fibers", refers to small diameter fibers which are formed by extruding a molten thermoplastic material as filaments from a plurality of fine, usually circular, capillaries of a spinneret with the diameter of the extruded filaments then being rapidly reduced as by, for example, eductive drawing or other well-known spunbonding mechanisms.

The term "finished absorbent article" is used herein to generally mean any absorbent article having incorporated all layers of material and other features that the article is intended to have which affect the product's performance characteristics. This term includes, but is not limited to, products well known in the art as diapers, sanitary napkins, and adult incontinent briefs.

The term "insult" is used herein to refer to the act of applying a finite amount of liquid to the topsheet of a finished absorbent article. An insult may occur during product use and during finished product testing. Consequently, "multiple insults" occur when the same finished absorbent article is insulted more than once. Multiple insults may occur during product use and during finished product testing.

As used herein, "unconsolidated" means the fibers have some freedom of movement and are not fixed in position with respect to the other fibers in the web. In other words, the fibers generally are not compacted together or fused to the extent that an aperture cannot close, rather, the aperture may be blocked by some fiber strands which extend across, and partially obstruct it.

As used herein, "consolidated" means the fibers are generally compacted, fused, or bonded, so as to restrict movement of the fibers individually. Consolidated fibers will generally not extend out into an aperture and will likely be more dense than unconsolidated fibers.

As used herein "mesh count" means the number of holes per square centimeter. Therefore a material with a higher mesh would have more holes while a lower mesh would have fewer holes.

As used herein, the term "point bonding" means bonding one or more fabrics at a plurality of discrete points. For example, thermal point bonding generally involves passing one or more layers to be bonded between heated rolls, for example, an engraved pattern roll and a smooth calender roll. The engraved roll is patterned in some way so that the entire fabric is not bonded over its entire surface, and the calender roll is usually smooth. As a result, various patterns for engraved rolls have been developed for functional as well as aesthetic reasons.

As used herein, "gsm" is an abbreviation for grams per square meter.

As used herein, "wetback" is a measure of fluid returning to the surface of an absorbent article as defined in EDANA test method 150.1.

Test Methods

Absorbency rate data are measured using EDANA test method 150.3. Wetback data are measured using EDANA test method 150.1.

Absorbent Article Embodiments

Figure 2:
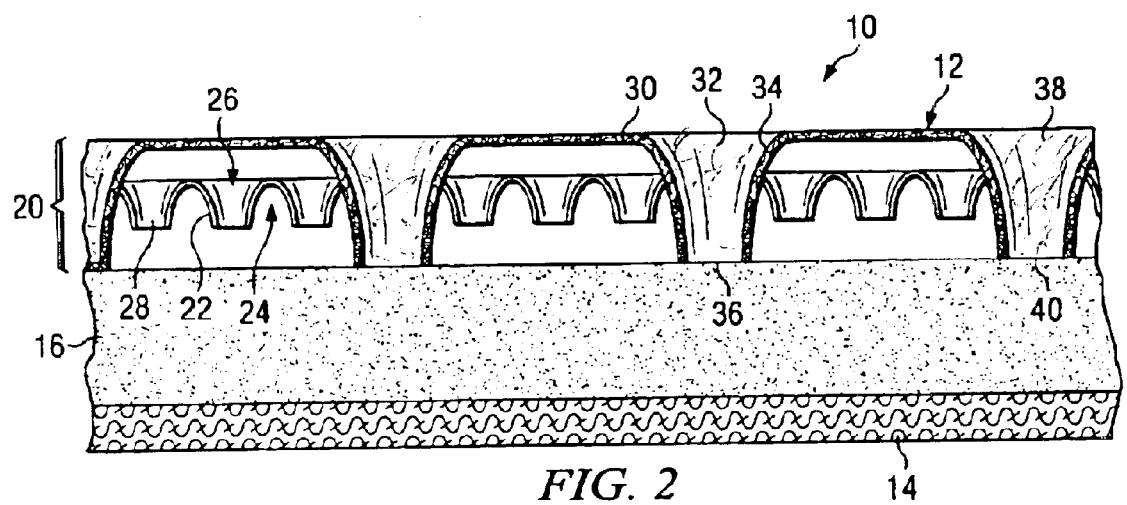
FIG. 2 is a cross sectional view of a second embodiment of the absorbent article of the invention.
Figure 3:
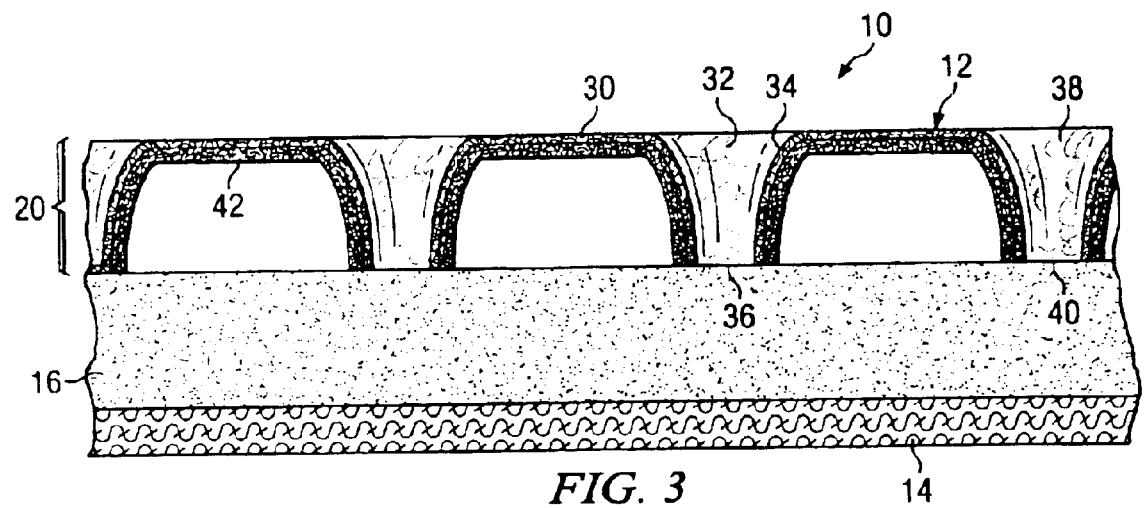
FIG. 3 is a cross sectional view of a third embodiment of the absorbent article of the invention.

Referring to FIG. 1, FIG. 2, and FIG. 3, absorbent article 10 has a body facing side 12. In use, the absorbent article 10 is typically placed so that body facing side 12 faces the user's body and the opposite side of the absorbent article is either exposed, as in a bandage, or faces the user's clothing, as in a diaper or feminine hygiene product. Backsheet 14 is opposite body facing side 12 and will typically be a fluid resistant or fluid impervious layer to prevent fluids from escaping the absorbent article 10. Absorbent core 16 will be between backsheet 14 and body facing side 12 to absorb fluids. Composite topsheet 20 will be between absorbent core 16 and body facing side 12. Composite topsheet 20 is designed to promote fluid flow from body facing side 12 to absorbent core 16 while also preventing fluid flow from absorbent core to body facing side 12, as discussed in the background and in the testing section below.

In FIG. 1 and FIG. 2 the composite topsheet 20 has a resilient three dimensional formed film 22 with a male side 24 and a female side 26. Small scale apertures 28 in the formed film 22 have a mesh count of between about $20/cm^2$ and $200/cm^2$. More preferably the mesh count of the small scale apertures is between about $50/cm^2$ and $100/cm^2$. Most preferably the mesh count of the small scale apertures is about $90/cm^2$. Formed film 22 is preferably made of a thermoplastic material to aid in forming. More preferably, formed film 22 is made of polypropylene, polyethylene, or some other polyolefin.

The resilient three dimensional shape of the formed film 22 creates a void volume on both the male side and the female side of the formed film 22. It is advantageous in this invention to maintain that void volume and not allow the absorbent core 16 or the fibers from the nonwoven web 30 to fill the void volume. The void volume allows for efficient fluid transfer both above and below the formed film. Therefore a light tissue may be placed between the absorbent core and the composite topsheet 20 to help in maintaining void volume of the composite topsheet.

A nonwoven web 30 is attached to the formed film 22 between the formed film 22 and on the body facing side 12. Nonwoven web 30 is preferably comprised of fibers of polymeric material, although other fibers may be used. In particular, polypropylene and polyethylene, either alone or in bi-component and other blends are effective.

A plurality of large scale apertures 32 extend through nonwoven web 30 and formed film 22. The large scale apertures 32 have a mesh that is less than the mesh of the small scale apertures 28. The mesh count of large scale apertures 32 will preferably be between $2/cm^2$ and $50/cm^2$, more preferably between $3/cm^2$ and $30/cm^2$, and most preferably between $6/cm^2$ and $11/cm^2$. Therefore, the small scale apertures 28 will be more numerous in a given area than the large scale apertures 32.

In the preferred embodiments shown in FIG. 1 and FIG. 2, the large scale apertures are generally conical, having a larger opening 34 and a smaller opening 36. In particular, the larger opening 34 is between the body facing side 12 and the smaller opening 36. In a more preferred embodiment there are substantially unconsolidated fibers 38 near the larger opening and substantially consolidated fiber 40 near the smaller opening.

In the preferred embodiments shown in FIGS. 1 and 2, the substantially consolidated fibers 40 and the formed film 22 are fused to create a point bond between the nonwoven web 30 and the formed film 22 at a plurality of the large scale apertures 32.

In the preferred embodiment shown in FIG. 1, the male side 24 of the formed film 22 is facing the nonwoven web 30. In contrast, FIG. 2 shows an embodiment where the female side 26 of the formed film 22 is facing the nonwoven web 30.

In a preferred embodiment the side of formed film 22 which is facing the nonwoven web 30, the male side 24 in FIG. 1 or the female side in FIG. 2, is treated with a surfactant, and therefore is more hydrophilic. Typical surfactants would include non-ionic and silicone based surfactants, although others may be used.

In FIG. 3 the composite topsheet 20 includes a stiffer nonwoven layer 42 in the place of formed film 22. The stiffer nonwoven layer 42 has a relatively rough texture, as compared to nonwoven web 30, and is formed of fibers with an average diameter larger than the fibers of nonwoven web 30. The stiffer nonwoven layer 42 is formed of materials similar to those used in nonwoven layer 30. The stiffer nonwoven layer 42 may be a separate nonwoven web joined with nonwoven web 30 in a manner similar to formed film 22, or it may be a layer of fibers formed with nonwoven web 30. The discussion above regarding the formation of large scale apertures 32 applies to the composite topsheet 20 of FIG. 3, with the stiffer nonwoven layer 42 replacing the formed film 22.

Method for Making Nonwoven-Film Composite

A formed film 22 is manufactured to have a resilient three dimensional structure. The film is preferably manufactured by a vacuum forming process, wherein a molten layer of thermoplastic material is fed from a melt die onto a shaped screen utilizing vacuum pressure to form the thermoplastic material to the shape of the screen. Other methods for manufacturing resilient three dimensional formed films may include reheat processes.

A nonwoven web 30 is manufactured from polymeric fibers. In a preferred embodiment the nonwoven web is airthrough bonded, carded thermobonded, spunbonded, or spunbond meltblown spunbond. In a preferred embodiment the fibers are single component or bi-component. In a preferred embodiment the material is polypropylene or polyethylene, although polyester may be added.

The formed film 22 and nonwoven web 30 are joined prior to forming of the large scale apertures 32. In a preferred embodiment the formed film 22 and the nonwoven web 30 are aligned adjacent each other. In another preferred embodiment the formed film 22 is adhesively secured to the nonwoven web 30 prior to the forming of large scale apertures 32. The importance of joining the nonwoven web 30 with the formed film 22 is so that large scale apertures 32 penetrate both the nonwoven web 30 and the formed film 22.

Figure 4:
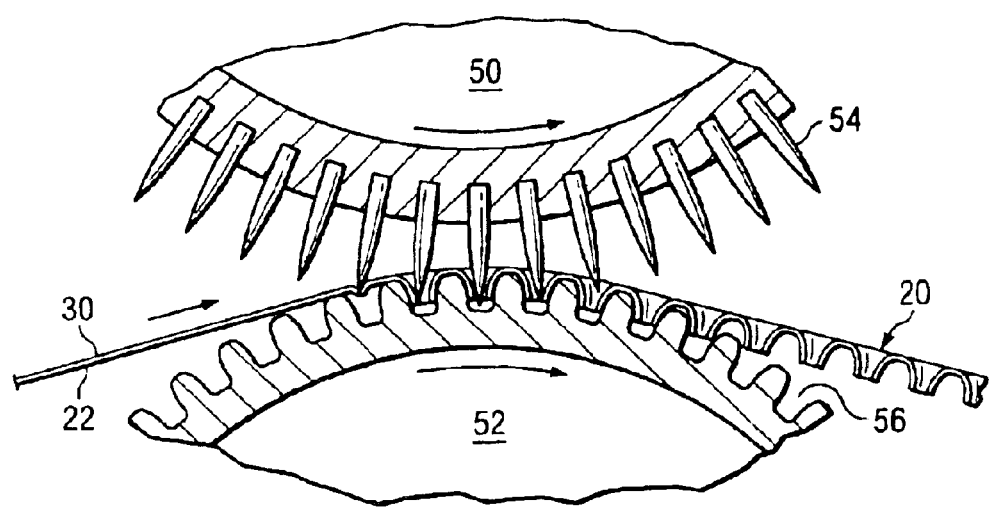
FIG. 4 is a cross sectional view of the method for manufacturing a composite topsheet.

FIG. 4 shows a preferred mechanism for forming large scale apertures 32. A pin roll 50 and counter roll 52 rotate in opposite directions to form a nip through which the nonwoven web 30 and formed film 22 are fed. Pins 54 protrude from the surface of pin roll 50. Holes 56 are recessed into counter roll 52. Pin roll 50 and counter roll 52 are aligned so that pins 54 mate with holes 56.

In a more preferred embodiment, pin roll 50 and counter roll 52 are manufactured of rigid material and are mounted on an adjustable chassis to allow modification of the distance between the rolls. In particular, pin roll 50 is preferably manufactured of metallic material and pins 54 are preferably manufactured of a metallic material. Pins 54 preferably have a pointed end and taper from about half of their length to the pointed end. In a preferred embodiment pins 54 are heated, as discussed in more detail below.

The holes 56 are preferably larger than pins 54 and are shaped. In a preferred embodiment the shape of holes 56 is partially replicated by the large scale apertures 32. In a preferred embodiment the holes 54 are generally conical so that when the pins 54 push material into holes 56 the material near the tips of pins 54 is compressed further than any other material, and experiences more heat transfer if the pins 54 are heated. This preferred combination of narrow heated pins 54 and generally conical holes 56 produces a preferred large scale aperture 32 having generally consolidated fibers 40 near a smaller opening 36 and generally unconsolidated fibers 38 near a larger opening 34.

In a less preferred embodiment counter roll 52 may be manufactured of a pliable material, thereby making holes 56 unnecessary. In such an embodiment pins 54 would simply protrude into the pliable material of counter roll 52.

The pins 54 may be heated for several reasons. One reason to heat pins 54 is to properly form large scale apertures 32. The heated pins 54 may also be heated to a temperature sufficient to bond the nonwoven web 30 to the formed film 22. Furthermore, the heated pins 54 may help in creating substantially consolidated fibers 40 near the smaller openings 36. The pins may also be heated to provide for structural resilience in large scale apertures 32 in order to maintain void volume between the composite topsheet 20 and the absorbent core 16. In particular, the heated pins may cause the formed film 22 or the stiffer nonwoven layer 42 to become more rigid and support the large scale apertures 32 during further processing, storage, or use. This allows the use of a softer nonwoven web 30 without compromising the shape of the large scale apertures 32 or the void volume they create between the composite topsheet 20 and the absorbent core 16.

In a first preferred embodiment the pins 54 are heated to a temperature sufficient to fuse the consolidated fibers 40 and the formed film 22 near the smaller openings 36, thus securing the nonwoven web 30 to the formed film 22. Even at this temperature, the shape of the pins 54 and the holes 56 is such that unconsolidated fibers 38 still exist near the large openings 34.

In another preferred embodiment the nonwoven web 30 is comprised of materials with more than one melting point, such that a plurality of fibers have a melting point near the melting point of the material of formed film 22, and lower than other fibers in the nonwoven web 30. The pins 54 are heated to a temperature to melt the lower melting point fibers and the formed film 22 near the smaller openings 36, thus forming consolidated fibers 40 and securing the nonwoven web 30 to the formed film 22.

In yet another embodiment the fibers of the nonwoven web 30 have a melting point that is higher than the melting point of the material of the formed film 22. The pins 54 are heated to a temperature sufficient to melt the formed film 22 and bond the consolidated fibers 40 near the smaller opening 36, thereby securing the nonwoven web 30 to the formed film 22.

In yet another preferred embodiment the nonwoven web 30 is secured to the formed film 22 prior to forming the large scale apertures. Preferably the securing would be an adhesive bonding. In this embodiment the pins 54 are heated to a temperature sufficient to shape the nonwoven web 30 in the vicinity of the large scale apertures and form consolidated fibers 40 near the smaller opening 36, but not necessarily enough to fuse the consolidated fibers 40 to the formed film 22, or the formed film 22 to the nonwoven web 30.

In yet another preferred embodiment the formed film any of the above examples is replaced with a stiffer nonwoven layer 42 with similar material characteristics.

Feminine Hygiene Finished Article Testing

The performance of a preferred embodiment of composite topsheet 20 was evaluated in use on an assembled LAURIER slim napkin. The embodiment tested had the male side 24 facing the body facing side 12 as shown in FIG. 2. Additionally the male side 24 was treated with an surfactant, in particular Silastol PST, produced by Schill & Seilacher. The nonwoven web in this example was a 16 gsm bi-component polypropylene/polyethylene nonwoven web. The composite topsheet 20 was bonded in the formation of the large scale apertures.

The cover was removed from a finished article and replaced with the example of composite topsheet 20 discussed above. A second finished article was tested as bought for comparison purposes.

The napkins were then tested with a 15 ml insult of saline solution, corresponding to 10 hours of use at an average flow of 1.45 ml/h, according to Nonwoven World, April–May, 2000. The absorbency rate and wetback were then measured.

The unmodified napkin had an absorbency rate of 16.77 seconds and a wetback of 2.67 grams while the napkin using composite topsheet 20 had a absorbency rate of 10.75 and a wetback of 0.14. This represents a 36% improvement in absorbency rate and a 95% improvement in wetback.

Feminine Hygiene Raw Material Testing

Raw material testing of a preferred embodiment of the composite topsheet 20 was performed to compare with other materials in the industry. In particular, the embodiment tested had the male side 24 facing the body facing side 12 as shown in FIG. 2. Additionally the male side 24 was treated with a surfactant, in particular Silastol PST, produced by Schill & Seilacher. The nonwoven web in this example was a 16 gsm bi-component polypropylene/polyethylene nonwoven web. The composite topsheet 20 was bonded in the formation of the large scale apertures. This was tested against the apertured nonwoven topsheet from a LAURIER Slim 20.5 cm napkin and the apertured nonwoven and acquisition distribution layer from a LAURIER 22.5 cm napkin.

The composite topsheet 20 of this invention had an absorbency rate of 1.21 seconds and a wetback of 0.09 grams while the LAURIER apertured nonwoven had a absorbency rate of 1.72 and a wetback of 0.21, and the LAURIER apertured nonwoven with an acquisition distribution layer had an absorbency rate of 1.58 seconds and a wetback of 0.15 grams. This shows a 23%–30% improvement in absorbency rate and a 40%–57% improvement in wetback.

Diaper Finished Article Testing

The performance of a preferred embodiment of composite topsheet 20 was evaluated in use on an assembled White Cloud baby diaper. The embodiment tested had the male side 24 facing the body facing side 12 as shown in FIG. 2. Additionally the male side 24 was treated with a surfactant, in particular Silastol PST, produced by Schill & Seilacher. The nonwoven web in this example was a 16 gsm bi-component polypropylene/polyethylene nonwoven web. The composite topsheet 20 was bonded in the formation of the large scale apertures.

The cover was removed from a finished article and replaced with the example of composite topsheet 20 discussed above. A second finished article was tested as bought for comparison purposes.

The diapers were then tested with three insults each according to the EDANA test methods mentioned above. The absorbency rate and wetback were then measured for each insult.

The unmodified diaper had absorbency rates of 45.9 s, 267.4 s and 327.7s for the three insults, while the diaper using the composite topsheet 20 had absorbency rates of 15.6 s, 34.9 s, and 56.3 s, showing an improvement of 66%, 87% and 82%, respectively for the three insults. The wetback measurements showed equal performance for the first two insults and a slight improvement for the third insult.

Conclusion

While the present invention has been described in detail with respect to specific embodiments thereof, it will be appreciated that those skilled in the art may readily conceive alterations to, variations of, and equivalents to those embodiments. The scope of the present invention should therefore be determined by the appended claims and equivalents thereto.

We claim:

1. An absorbent article with a body facing side, the absorbent article comprising:
    a backsheet opposite the body facing side;
    an absorbent core between the backsheet and the body facing side; and
    a composite topsheet between the absorbent core and the body facing side, said composite topsheet comprising:
        a resilient three-dimensional apertured formed film between the absorbent core and the body facing side, said formed film having a male side with protrusions and a female side with lands opposite the male side, and small scale apertures having a mesh count;
        a nonwoven web of fibers between the formed film and the body facing side of the absorbent article; and
        a plurality of three-dimensional conical shaped apertures in the nonwoven layer that extend through the formed film, said apertures having a mesh count which is less than the mesh count of the small scale apertures.

2. The absorbent article of claim 1 wherein the male side of the formed film faces the nonwoven web.

3. The absorbent article of claim 1 wherein the female side of the formed film faces the nonwoven web.

4. The absorbent article of claim 1 wherein said three-dimensional conical shaped apertures in the nonwoven layer taper from a larger opening to a smaller opening, the larger opening being between the smaller opening and the body facing side.

5. The absorbent article of claim 4 wherein the nonwoven layer has generally unconsolidated fibers near the larger opening and generally consolidated fibers near the smaller opening.

6. The absorbent article of claim 4 wherein fibers of said nonwoven web are bonded at said smaller opening by melted portions of said formed film.

7. The absorbent article of claim 1 wherein the mesh count of the small scale apertures is between about 20 apertures/$cm^2$ and about 200 apertures/$cm^2$.

8. The absorbent article of claim 1 wherein the mesh count of the small scale apertures is between about 50 apertures/$cm^2$ and about 100 apertures/$cm^2$.

9. The absorbent article of claim 1 wherein the mesh count of the small scale apertures is about 90 apertures/$cm^2$.

10. The absorbent article of claim 1 wherein the mesh count of the apertures in the nonwoven is between about 2 apertures/$cm^2$ and about 50 apertures/$cm^2$.

11. The absorbent article of claim 1 wherein the mesh count of the apertures in the nonwoven is between about 3 apertures/$cm^2$ and about 30 apertures/$cm^2$.

12. The absorbent article of claim 1 wherein the mesh count of the apertures in the nonwoven is between about 6 apertures/$cm^2$ and about 11 apertures/$cm^2$.

13. The absorbent article of claim 1 wherein the mesh count of the small scale apertures is between about 5 and about 25 times the mesh count of the apertures in the nonwoven.

14. The absorbent article of claim 1 wherein the mesh count of the small scale apertures is between about 10 and about 20 times the mesh count of the apertures in the nonwoven.

15. The absorbent article of claim 1 wherein the mesh count of the small scale apertures is about 15 times the mesh count of the apertures in the nonwoven.

16. The absorbent article of claim 1 wherein the nonwoven web is selected from the group consisting of an airthrough bonded nonwoven, a carded thermobonded nonwoven, and a spunbond meltblown spunbond nonwoven.

17. The absorbent article of claim 1 wherein the nonwoven web is selected from the group consisting of polypropylene fibers, polyethylene fibers, and a combination of polypropylene and polyethylene fibers.

18. The absorbent article of claim 1 wherein the nonwoven web is comprised of polyester fibers.

19. The absorbent article of claim 1 wherein the formed film is comprised of low density polyethylene.

20. The absorbent article of claim 1 wherein the body facing side of the formed film is coated with a surfactant.

21. A composite topsheet comprising a resilient three-dimensional apertured formed film, said formed film having a male side with protrusions and a female side with lands opposite the male side, and small scale apertures having a mesh count; a nonwoven web of fibers; and a plurality of three-dimensional conical shaped apertures in the nonwoven layer that extend through the formed film, said apertures having a mesh count which is less than the mesh count of the small scale apertures, made by a method comprising:
    forming a resilient three dimensional apertured formed film having a male side and a female side, said formed film being formed with small scale apertures having a mesh count;
    forming a nonwoven web of fibers;
    joining the nonwoven web with the apertured formed film; and
    aperturing the joined nonwoven web and formed film to create three-dimensional conical shaped apertures in the joined nonwoven web and formed film, a plurality of said three-dimensional conical shaped apertures in the nonwoven layer created at a mesh count that is less than the mesh count of the small scale apertures.

22. The composite topsheet of claim 21 wherein the forming of the resilient three dimensional apertured formed film is performed by vacuum forming of the film.

23. The composite topsheet of claim 21 wherein the forming of the nonwoven web of fibers is formed by one of airthrough bonding, carded thermobonding, or spunbond meltblown spunbonding.

24. The composite topsheet of claim 1 wherein the joining of the nonwoven web to the formed film includes the addition of an adhesive between the nonwoven web and the formed film.

25. The composite topsheet of claim 1 wherein the aperturing of the joined nonwoven web and formed film secures the nonwoven web to the formed film.

26. The composite topsheet of claim 25 wherein the nonwoven web is secured to the formed film by the fusing of the fibers of the nonwoven web to portions of the formed film at the three-dimensional conical shaped apertures in the nonwoven layer.

27. The composite topsheet of claim 25 wherein the nonwoven web is secured to the formed film by the melting of the formed film near the three-dimensional conical shaped apertures in the nonwoven layer.

28. The composite topsheet of claim 25 wherein the nonwoven web is secured to the formed film by the melting of a plurality of the fibers in the nonwoven web near the three-dimensional conical shaped apertures in the nonwoven layer.

29. The composite topsheet of claim 21 wherein a three-dimensional conical shaped apertures in the nonwoven layer is formed by a heated needle mating into a shaped recess such that the apertures are resilient three dimensional.

30. The composite topsheet of claim 29 wherein the three-dimensional conical shaped apertures in the nonwoven layer is shaped by a contacting surface of the needle and the shaped recess such that the fibers of the nonwoven web are selectively fused only in the vicinity of the contacting surface.

31. An absorbent article with a body facing side, the absorbent article comprising:
    a backsheet opposite the body facing side;
    an absorbent core between the backsheet and the body facing side; and
    a composite topsheet between the absorbent core and the body facing side, said composite topsheet comprising:
        a stiffening means between the absorbent core and the body facing side, said stiffening means having openings with a hydraulic radius;
        a nonwoven web of fibers between the stiffening means and the body facing side of the absorbent article, said nonwoven web of fibers having an average radius of the fibers; and
        a plurality of three-dimensional conical shaped apertures in the nonwoven layer that extend through the stiffening means, said apertures having a hydraulic radius which is substantially greater than the hydraulic radius of the openings of the stiffening means.

32. The absorbent article of claim 31 wherein the stiffening means comprises a resilient three-dimensional apertured formed film between the absorbent core and the body facing side, said formed film having a male side and a female side opposite the male side.

33. The absorbent article of claim 31 wherein the stiffening means comprises a stiffer nonwoven layer of fibers having a larger average radius of fibers.

* * * * *